US012740870B2

(12) United States Patent
Bray, Jr. et al.

(10) Patent No.: US 12,740,870 B2
(45) Date of Patent: Sep. 22, 2026

(54) IMPLANT INCLUDING EGG-SHAPED INTERNAL ARCHITECTURE, AND METHODS

(71) Applicants: Robert S. Bray, Jr., Newport Beach, CA (US); Robert P. Kenney, La Verne, CA (US)

(72) Inventors: Robert S. Bray, Jr., Newport Beach, CA (US); Robert P. Kenney, La Verne, CA (US)

( * ) Notice: Subject to any disclaimer, the term of this patent is extended or adjusted under 35 U.S.C. 154(b) by 0 days.

(21) Appl. No.: 19/326,897

(22) Filed: Sep. 12, 2025

(65) Prior Publication Data

US 2026/0183119 A1 Jul. 2, 2026

Related U.S. Application Data

(60) Provisional application No. 63/740,173, filed on Dec. 30, 2024.

(51) Int. Cl.
*A61F 2/44* (2006.01)
*A61F 2/30* (2006.01)

(52) U.S. Cl.
CPC ........ *A61F 2/4455* (2013.01); *A61F 2/30767* (2013.01); *A61F 2002/3093* (2013.01); *A61F 2002/4435* (2013.01); *A61F 2/447* (2013.01); *A61F 2220/0008* (2013.01); *A61F 2230/0008* (2013.01); *A61F 2230/0076* (2013.01); *A61F 2250/0036* (2013.01); *A61F 2250/0037* (2013.01)

(58) Field of Classification Search
CPC .... A61F 2/4455–447; A61F 2230/0008; A61F 2230/0076; A61F 2002/30754
See application file for complete search history.

(56) References Cited

U.S. PATENT DOCUMENTS

| | | | |
|---|---|---|---|
| 6,206,924 | B1 | 3/2001 | Timm |
| 7,550,008 | B2 | 6/2009 | Ralph et al. |
| 8,551,173 | B2 | 10/2013 | Lechmann et al. |
| 10,368,997 | B2 | 8/2019 | Jones et al. |
| 10,507,118 | B2 | 12/2019 | Afzal |
| 10,575,965 | B2 | 3/2020 | Kim et al. |
| 10,695,192 | B2 | 6/2020 | Bishop et al. |
| 11,160,668 | B2 | 11/2021 | Nyahay et al. |

(Continued)

FOREIGN PATENT DOCUMENTS

| | | |
|---|---|---|
| CN | 106618809 A | 5/2017 |
| CN | 107411855 A | 12/2017 |

(Continued)

OTHER PUBLICATIONS

International Search Report for PCT/US2025/060368 dated May 6, 2026.

*Primary Examiner* — Rebecca S Preston
(74) *Attorney, Agent, or Firm* — PK Patent Law

(57) ABSTRACT

A surgical implant includes an interior architecture including at least one ovate or egg-shaped bone contacting element. The at least one egg-shaped bone contacting element being defined by a first wall structure including a superior side portion, intermediate portions, and an inferior side portion. The superior side portion includes a top end defining a first arc radius and the inferior side portion includes a bottom end defining a second arc radius. The first arc radius is smaller than the second arc radius.

13 Claims, 8 Drawing Sheets

(56) References Cited

U.S. PATENT DOCUMENTS

| | | | | |
|---|---|---|---|---|
| 11,174,911 | B2 | 11/2021 | Kang et al. | |
| 11,185,423 | B2 | 11/2021 | Tipping | |
| 11,612,494 | B2 | 3/2023 | Mazur et al. | |
| 11,679,181 | B2 | 6/2023 | Kerr et al. | |
| 11,793,652 | B2 | 10/2023 | Sack | |
| 11,819,419 | B2 | 11/2023 | Hamzey et al. | |
| 11,938,039 | B2 | 3/2024 | Bishop et al. | |
| 12,042,397 | B2 | 7/2024 | Sekhon | |
| 12,097,123 | B2 | 9/2024 | McShane, III et al. | |
| 12,102,544 | B2 | 10/2024 | Hodrinsky et al. | |
| 2013/0123935 | A1 | 5/2013 | Hunt et al. | |
| 2017/0319344 | A1 | 11/2017 | Hunt | |
| 2018/0228617 | A1* | 8/2018 | Srour | A61F 2/4611 |
| 2021/0338454 | A1 | 11/2021 | Afzal | |
| 2022/0054713 | A1 | 2/2022 | Nakano et al. | |
| 2023/0165690 | A1 | 6/2023 | Blain et al. | |
| 2023/0277321 | A1* | 9/2023 | Link | A61F 2/34 623/23.5 |

FOREIGN PATENT DOCUMENTS

| | | | |
|---|---|---|---|
| CN | 110584845 | A | 12/2019 |
| CN | 112674917 | B | 8/2021 |
| CN | 117653426 | A | 3/2024 |
| EP | 3389570 | B1 | 4/2024 |
| EP | 4450030 | A2 | 10/2024 |
| KR | 10-1960952 | B1 | 3/2019 |
| KR | 102151554 | | 9/2020 |
| WO | 2017106780 | A1 | 6/2017 |
| WO | 2023027472 | A1 | 2/2023 |

* cited by examiner 700
750
400
400
400

700
750
400
400
400

750
700
400
400

IMPLANT INCLUDING EGG-SHAPED INTERNAL ARCHITECTURE, AND METHODS

CROSS REFERENCE TO RELATED APPLICATION

The present application claims the benefit from earlier filed U.S. Provisional Patent Application Ser. No. 63/740,173, filed Dec. 30, 2024, which is incorporated herein in its entirety by reference.

FIELD OF THE INVENTION

The present teachings generally relate to implants for supporting bone growth in a patient.

BACKGROUND OF THE INVENTION

A variety of different implants are used in the body. Implants used in the body to stabilize an area and promote bone ingrowth provide both stability (i.e. minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain.

In preparation for an anterior spinal fusion, most of the intervertebral disc is removed. An implant, the spinal fusion cage, may be placed between the vertebra to maintain spine alignment and disc height. The fusion, i.e. bone bridge, occurs between the endplates of the vertebrae.

However, providing space within the implant for the bone ingrowth can compromise the strength and stability of the implant. In addition, increasing the peripheral area of the implant compromises the surface area for fusion and reduces the effectiveness of the implant.

There is a need for improved implants that maintain their shape under pressure and tension and provide sufficient openings for bone ingrowth.

An object of the present invention is to provide improved implants.

It is a further object of the present invention to provide systems for repairing bone or creating bone fusion in a patient.

It is a still further object of the present invention to provide methods of manufacturing such implants.

SUMMARY OF THE INVENTION

The present teachings provide a surgical implant including an interior architecture including at least one egg-shaped bone contacting element. The at least one egg-shaped bone contacting element can be defined by a first wall structure including a superior side portion, intermediate portions, and an inferior side portion. The superior side portion can include a top end defining a first arc radius and the inferior side portion can include a bottom end defining a second arc radius. The first arc radius can be smaller than the second arc radius.

The present teachings also provide a surgical implant including an interior architecture including at least one egg-shaped bone contacting element. The at least one egg-shaped bone contacting element can be defined by a first wall structure including a superior side portion including a top end, intermediate portions, and an inferior side portion including a bottom end. The at least one egg-shaped bone contacting element can include a height measured from the top end to the bottom end of the wall structure and a width measured at a maximum distance directly across the intermediate portions. The height can be greater than the width.

The present teachings still further provide a surgical implant including an interior architecture including a plurality of egg-shaped bone contacting elements arranged in a three-dimensional structure. The plurality of egg-shaped bone contacting elements can include a superior side portion and an inferior side portion. The superior side portion of the egg-shaped bone contacting elements can form a domed superior contour surface and the inferior side portion of the egg-shaped bone contacting elements can form a domed inferior contour surface. The domed superior contour surface can be shaped differently from the domed inferior contour surface.

The present teachings still further provide a surgical implant including an interior architecture including at least one ovate-shaped bone contacting element. The at least one ovate-shaped bone contacting element can be defined by a first wall structure including a superior side portion, intermediate portions, and an inferior side portion. The superior side portion includes a top end and the inferior side portion includes a bottom end. The bottom end can be broader compared to the top end.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

It is to be understood that both the foregoing general description and the following detailed description are exemplary and explanatory only, and are intended to provide an explanation of various embodiments of the present teachings.

DETAILED DESCRIPTION OF THE PREFERRED EMBODIMENTS

Figure 1:
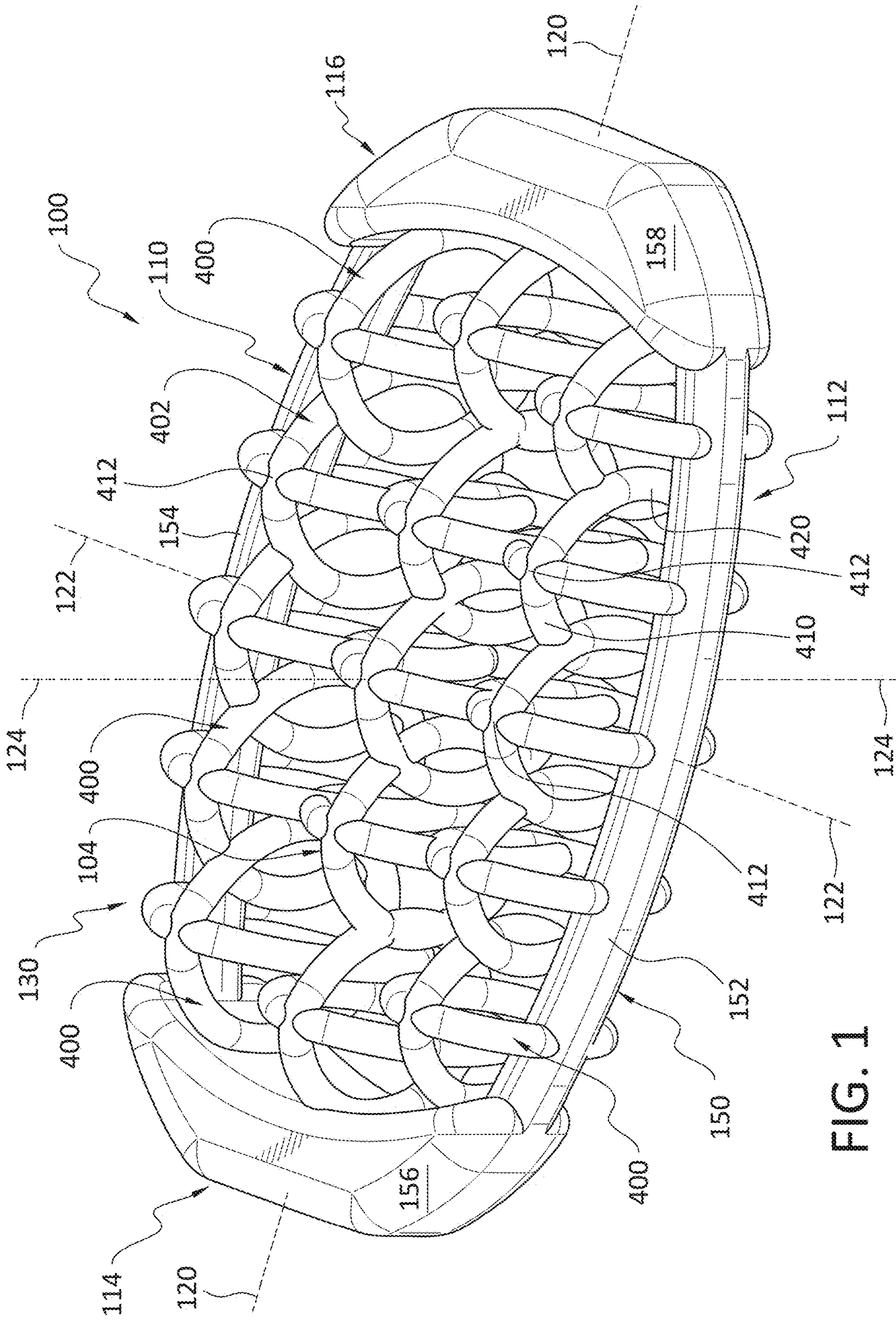
FIG. 1 is a trimetric view of an embodiment of the implant of the present teachings.

FIG. 1 shows an isometric view of an embodiment of implant 100 of the present teachings. Implant 100 can also be referred to as a cage or fusion device. In some embodiments, implant 100 can be configured to be implanted within a portion of the human body. In some embodiments, implant 100 can be configured for implantation into various portions of the spine. In some embodiments, implant 100 can be a spinal fusion implant, or spinal fusion device, that is inserted between adjacent vertebrae to provide support and/or facilitate fusion between the neighboring vertebrae.

According to various embodiments, implant 100 can include a body including an interior implant architecture 104 and a peripheral structure 150. The peripheral structure 150 can provide an exterior frame for implant 100 and can be optional.

According to various embodiments, the interior implant architecture 104 of the implant 100 can include a plurality of ovate or egg-shaped bone contacting elements 400. As will be discussed in more detail below and best shown in FIG. 3, the respective height, H, of each egg-shaped bone contacting element 400 can be greater than its width, W. In addition, the top end 412 of each egg-shaped bone contacting element 400 defines a smaller arc radius compared to the arc radius of its bottom end 442. The shape can be referred to as ovate or egg-shaped, where the bottom end 442 is broader compared to the top end 412.

The plurality of egg-shaped bone contacting elements 400 make up the interior implant architecture 104 of the implant 100. The plurality of egg-shaped bone contacting elements 400 can be attached, and/or continuously formed (or "integrally formed") with, the peripheral structure 150 of the implant 100. Alternatively, implant 100 can include an interior implant architecture 104 made up of the plurality of oval or egg-shaped bone contacting elements 400 without the peripheral structure.

As used herein, each egg-shaped bone contacting element 400 can define a distinctive member or element that spans a region or area of an implant. In some embodiments, a plurality of egg-shaped bone contacting elements 400 can overlap or intersect, like elements in a lattice or other 3D mesh structure. In some embodiments, the plurality of egg-shaped bone contacting elements 400 can form a three-dimensional structure. A series of neighboring egg-shaped bone contacting elements 400 overlap or intersect to form a substantially linear row that can span an area of implant 100, for example, the longitudinal and/or transverse dimensions of implant 100. The interior implant architecture 104 can be made up of a plurality of interesting rows of bone contacting elements 400. In some embodiments, not all the bone contacting elements 400 overlap or intersect and not all the bone contacting elements 400 need to possess an ovate or egg-shape. Moreover, not all elements 400 will operate to contact bone after surgical implantation of implant 100.

Each egg-shaped bone contacting element 400 can include a wall structure 402 having an approximately rounded or circular cross-sectional shape along at least a portion of the element 400 (i.e., the walls defining the element 400 can have the geometry of a solid tube). However, in other embodiments, the wall structure 402 of the egg-shaped bone contacting element 400 could have any other cross-sectional shape, including, but not limited to various polygonal cross-sectional shapes, as well as any other regular and/or irregular cross-sectional shapes. In some cases, for example, the cross-sectional shape of egg-shaped bone contacting element 400 could vary along the length of its wall structure 402 (e.g., the diameter or shape could change along its length).

For purposes of clarity, reference is made to various directional adjectives throughout the detailed description and in the claims. As used herein, the term "anterior" refers to a side or portion of implant 100 that is intended to be oriented towards the front of the human body when the implant has been placed in the body. Likewise, the term "posterior" refers to a side or portion of implant 100 that is intended to be oriented towards the back of the human body following implantation. In addition, the term "superior" refers to a side or portion of the implant 100 that is intended to be oriented towards a top (e.g., the head) of the body while "inferior" refers to a side or portion of the implant 100 that is intended to be oriented towards a bottom of the body. Reference is also made herein to "lateral" sides or portions of implant 100, which are sides or portions facing along lateral directions of the body following implantation.

In each of the figures, implant 100 is understood to be configured with an anterior side 110 and a posterior side 112. Implant 100 can also include a first lateral side 114 and a second lateral side 116 that extend between the posterior side 112 and the anterior side 110 on opposing sides of implant 100. Furthermore, implant 100 can also include a superior side 130 and an inferior side 140.

Reference is also made to directions or axes that are relative to the implant itself, rather than to its intended orientation with regards to the body. For example, the term "distal" refers to a part that is located further from the center of an implant, while the term "proximal" refers to a part that is located closer to the center of the implant. As used herein, the "center of the implant" could be the center of mass and/or a central plane and/or another centrally located reference surface.

An implant can also be associated with various axes. Referring to FIG. 1, implant 100 can be associated with a lateral axis 120 that extends along implant 100 between first lateral side 114 and second lateral side 116. Additionally, implant 100 can be associated with a posterior-anterior axis 122 that extends between posterior side 112 and anterior side 110. Moreover, implant 100 can be associated with a vertical axis 124 that extends along the thickness dimension of implant 100 and which is generally perpendicular to both lateral axis 120 and posterior-anterior axis 122.

An implant may also be associated with various reference planes or surfaces. As used herein, the term "median plane" refers to a vertical plane which passes from the anterior side 110 to the posterior side 112 of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about a plane, such as the median plane.

Peripheral Structure

According to various embodiments, the body of the implant 100 can include a peripheral structure 150. The peripheral structure 150 could include a ring, such as the geometry of a peripheral ring structure. The peripheral structure 150 can include any number of plates, walls, or similar structures. One or more support beams can extend from the peripheral structure 150.

Figure 2:
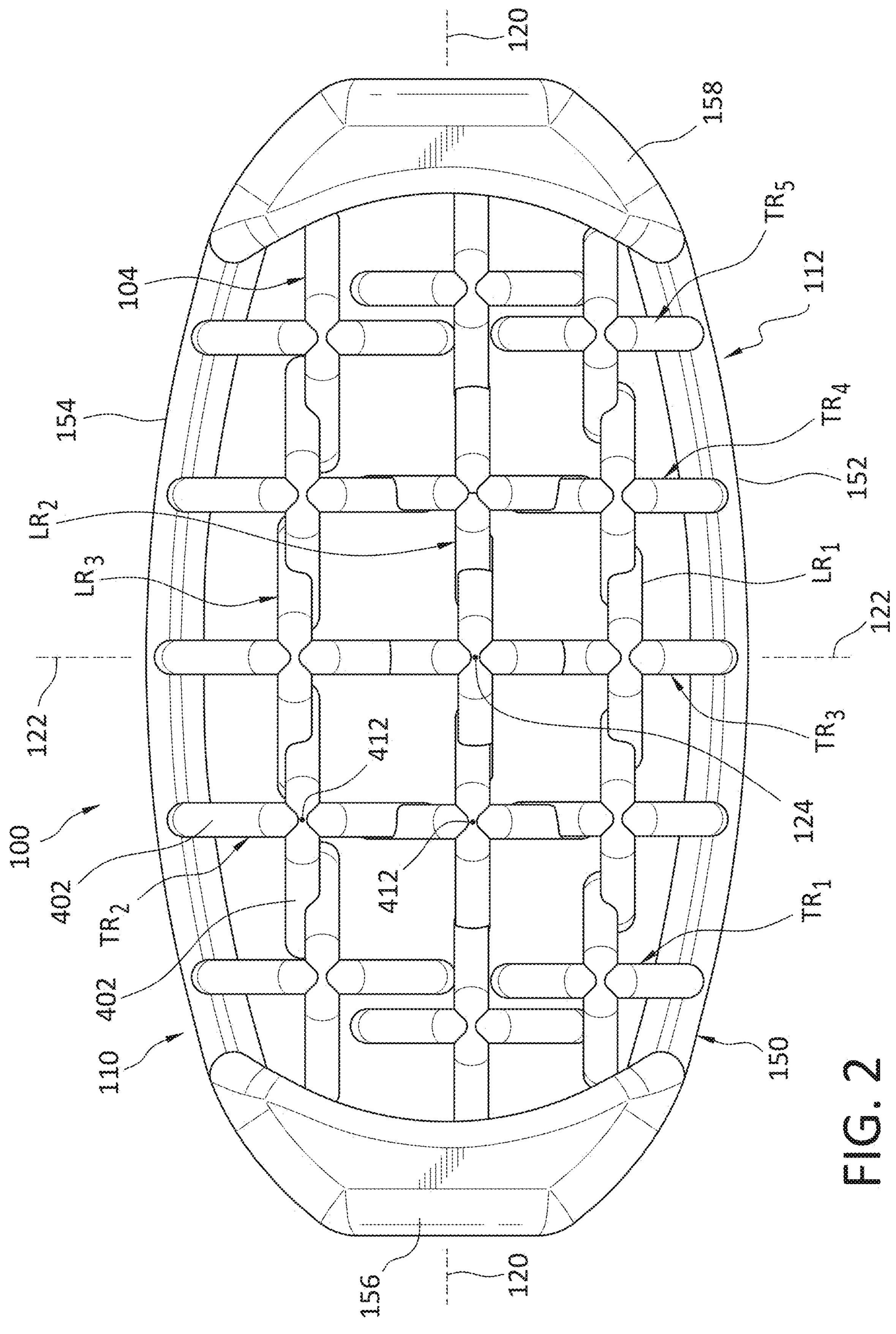
FIG. 2 is a top view of the implant of the present teachings.

For example, as best shown in FIGS. 1 and 2, the peripheral structure 150 can include a posterior cross-member 152 that can bow outwardly in a posterior direction. The peripheral structure 150 can also include an anterior cross-member 154 that can bow outwardly in an anterior direction. The peripheral structure 150 can also include a first lateral side plate 156 and a second lateral side plate 158. Each of the lateral side plates 156, 158 can include a bullet-shape on one end, or generally can be referred to as "bullet-shaped", to facilitate the implantation procedure into the spine. The implant 100 shown can be used in conjunction with an LLIF (Lateral Lumbar Interbody Fusion) procedure, which involves accessing the spine from the side of the body, removing a damaged disc, and then inserting the implant 100 in its place to promote bone growth and fusion. The implant 100 shown can also be used in conjunction with an OLIF (Oblique Lateral Interbody Fusion) procedure, which involves accessing the spine from a side approach, between the abdominal muscles and the psoas muscle, to fuse vertebrae together. No matter the direction from which the spine is assessed, the implant of the present teachings can also be provided with a threaded feature for attachment to an insertion tool, as well as pin holes to keep the clocking alignment. That is, the pin holes can allow temporary fixation by accommodating temporary fixation pins, which are used to hold the implant in its desired position on the vertebrae during the preliminary stages of surgery.

The peripheral structure 150 can be a continuous structure in which posterior cross-member 152 is connected to first lateral side plate 156, first lateral side plate 156 is connected to anterior cross-member 154, anterior cross-member 154 is connected to second lateral side plate 158, and second lateral side plate 158 is connected to posterior cross-member 152. That is, posterior cross-member 152, first lateral side plate 156, anterior cross-member 154, and second lateral side plate 158 together form a continuous or unbroken ring.

Egg-Shaped Bone Contacting Elements

According to various embodiments, each of the bone contacting elements 400 can include an ovate or egg-shaped external wall structure including a superior side portion 410, intermediate portions 420, and an inferior side portion 440. The intermediate portions 420 can each have an outwardly extending, arched geometry and can extend between the superior side portion 410 and the inferior side portion 440 of the bone contacting element 400.

Figure 3:
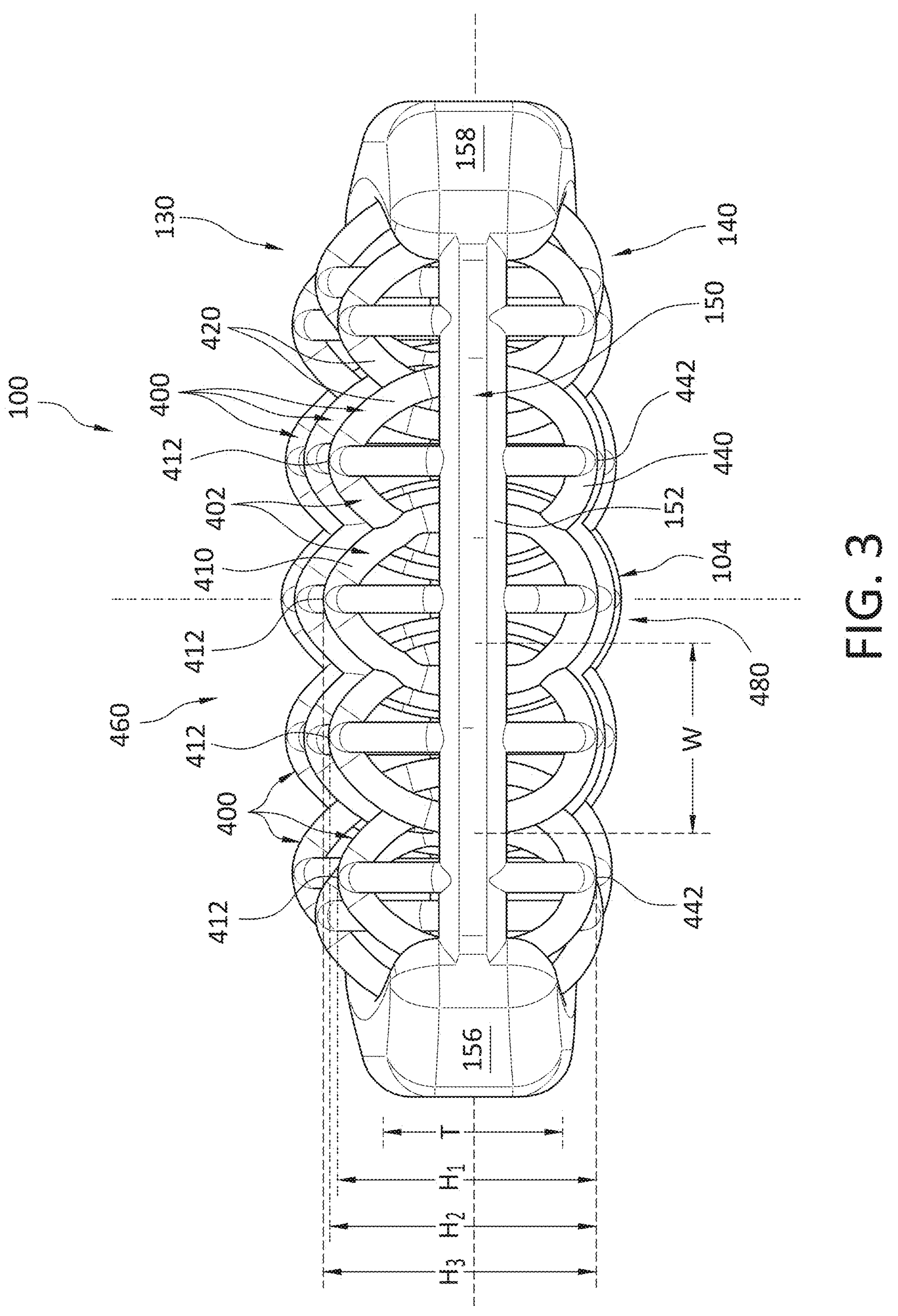
FIG. 3 is a front view (anterior) or back view (posterior) of the implant of the present teachings depending on the region of implantation in the spine.
Figure 4:
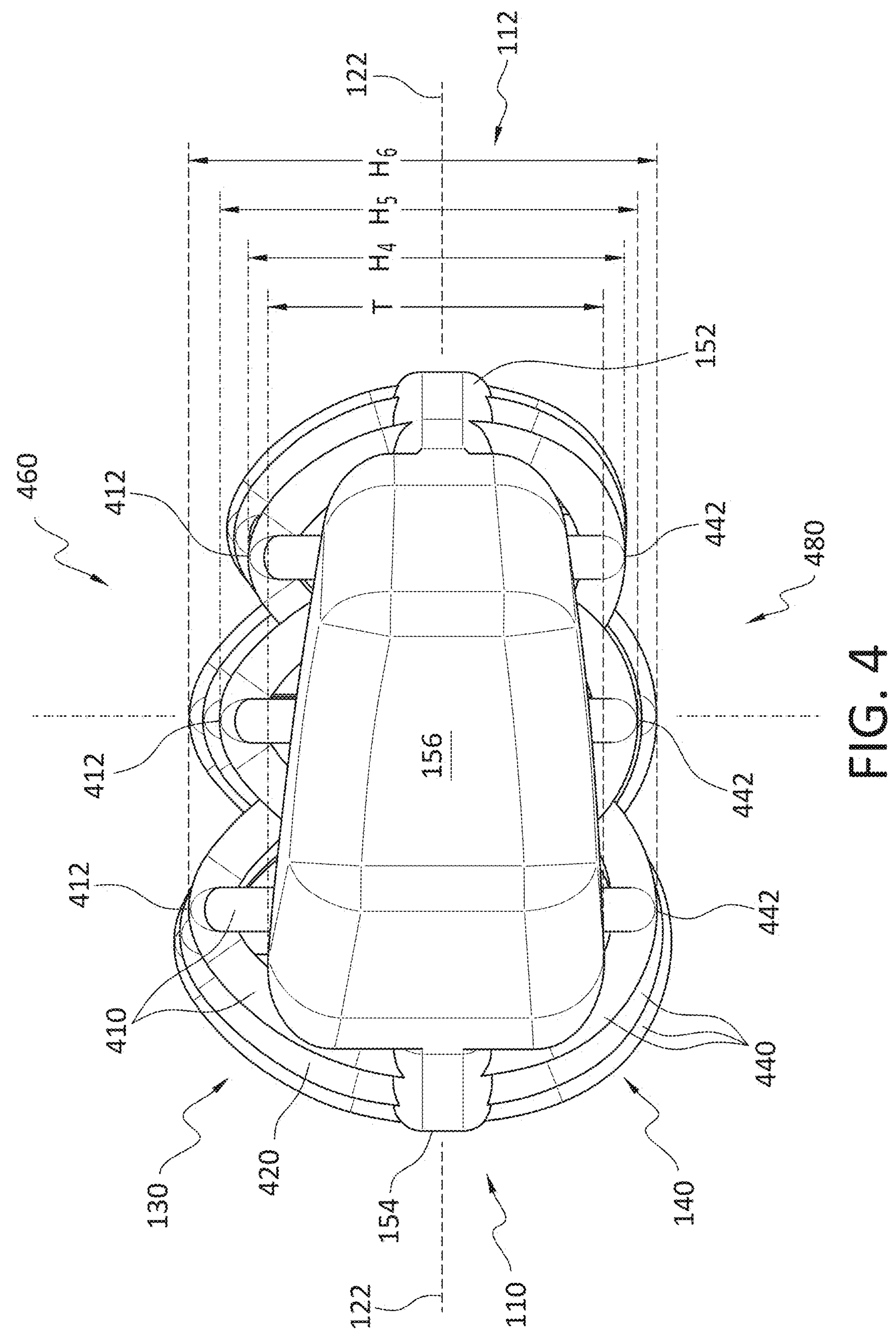
FIG. 4 is a side or lateral view of the implant of the present teachings.
Figure 5:
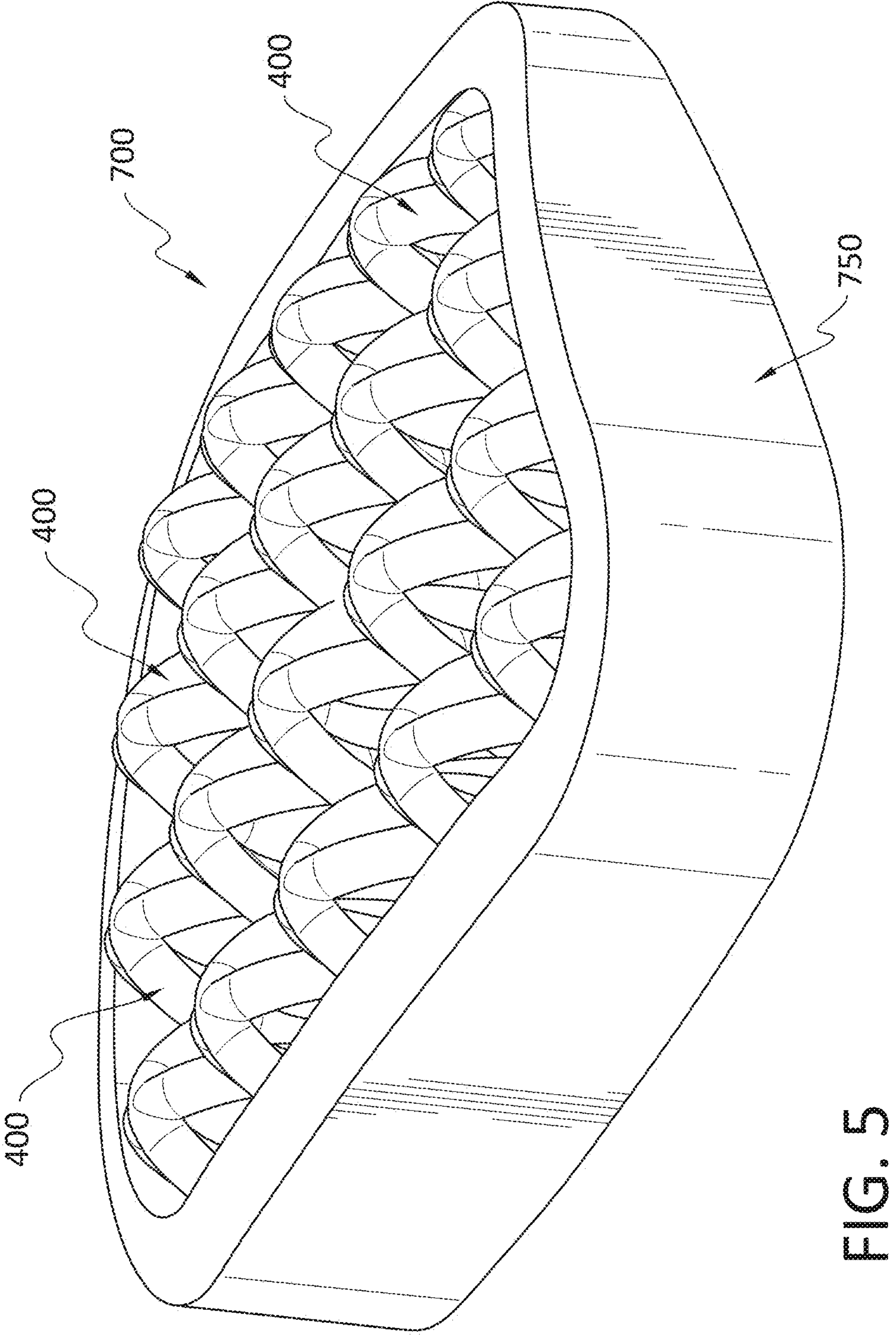
FIG. 5 is a trimetric view of another embodiment of the implant of the present teachings.

Referring to FIGS. 3 and 4, the superior side portion 410 of each egg-shaped bone contacting element 400 includes a top end 412. The top end 412 of the bone contacting element 400 can include an arc radius that is the smallest or tightest of the entire wall structure 402 making up the bone contacting element 400 (that is, the top end 412 defines a pointed top). Moving downwardly along the respective wall structures 402 from the superior side portion 410 to the arched intermediate side portions 420, the arc radius increases until reaching a point that defines the largest distance (i.e. measured laterally across the egg-shaped bone contacting element 400) between the intermediate side portions 420. This point is where the width, W, of the egg-shaped bone contacting element 400 can reach a maximum dimension as measured directly across (i.e. parallel to the ground) of the egg-shaped bone contacting element 400. At this area of the intermediate side portions 420, the arc radius can begin to slowly decrease as one moves further downwardly along the intermediate side portions 420 to the inferior side portion 440 until reaching a relatively flat bottom end 442 of the egg-shaped bone contacting element 400. The arc radius at the bottom end 442 of each egg-shaped bone contacting element 400 is larger than the arc radius at the top end 412. That is, the bottom end 442 of each egg-shaped bone contacting element 400 is flatter (or broader) relative to the "pointy" top end 412. This defines the ovate shape of the bone contacting element 400.

As best shown in FIGS. 1 and 2, a plurality of egg-shaped bone contacting elements 400 can be lined up in a series to create a row.

For example, one or more longitudinally extending rows of egg-shaped bone contacting elements 400 can extend along, or parallel with, the lateral axis 120 of the implant 100. As shown, three rows $LR_1$, $LR_2$, $LR_3$ of egg-shaped bone contacting elements 400 can extend along the longitudinal dimension of the implant 100 between the first lateral side plate 156 and the second lateral side plate 158.

Moreover, one or more transversely extending rows of egg-shaped bone contacting elements 400 can extend along, or parallel to, the posterior-anterior axis 122 of the implant 100. As shown, five rows $TR_1$, $TR_2$, $TR_3$, $TR_4$, $TR_5$ of egg-shaped bone contacting elements 400 can extend along the transverse dimension of the implant 100 between the posterior cross-member 152 and the anterior cross-member 154.

Accordingly, an egg-shaped bone contacting element 400 can be defined by an ovate or egg-shaped external wall structure that extends either generally longitudinally or laterally. Moreover, an egg-shaped bone contacting element 400 can be defined by a second ovate or egg-shaped external wall structure that intersects the first egg-shaped external wall structure. Both intersecting egg-shaped external wall structures 402 can share a top end 412 and a bottom end 442. For example, as best shown in FIG. 2 from a top view, the first egg-shaped external wall structure 402 can be arranged to extend substantially perpendicularly with respect to the second egg-shaped external wall structure, thereby forming a "+". According to various embodiments, an egg-shaped bone contacting element 400 can be defined by any number of intersecting egg-shaped external wall structures. The intersecting egg-shaped external wall structures can be equally angularly spaced from each other.

Multiple individual egg-shaped bone contacting elements 400 or multiple rows of egg-shaped bone contacting elements 400 can overlap or intersect to create a lattice or other 3D mesh structure making up the interior implant architecture 104 of the implant 100. While the egg-shaped bone contacting elements 400 can intersect or connect to each other for stability, when implanted each egg-shaped bone contacting element 400 is capable of bearing weight independently of any other bone contacting element 400. Accordingly, not all the egg-shaped bone contacting elements 400 are required to interconnect with each other. This allows the egg-shaped bone contacting elements 400 to fill the open area within any shape of peripheral structure 150. The interconnection of the egg-shaped bone contacting elements 400 as set forth in the present teachings provides an extremely stable interior implant architecture 104 that reduces or prevents the creation of stress risers in the middle of implant 100.

As will be discussed in more detail below and as best shown in FIGS. 3 and 4, the plurality of superior side portions 410 of the bone contacting elements 400 of implant 100 taken together form a domed superior contour surface 460. The ends 412 of the superior side portions 410 are configured to directly contact and cut into an upper vertebral endplate when implanted. Also, the plurality of inferior side portions 440 of the bone contacting elements 400 of implant 100 taken together form a domed inferior contour surface 480. The ends 442 of the inferior side portions 440 are configured to directly contact a lower vertebral endplate when implanted. Together, these differently shaped contour surfaces 460, 480 form domed-shaped bone contacting regions that can engage and cut into respective upper and lower vertebral body surfaces when implanted. As will be discussed in more detail below, differently shaped contour surfaces 460, 480 will cut into the respective upper and lower vertebral body surfaces at different rates based on an arc curve to achieve a selectively controlled subsidence.

Tops and Bottoms of Eggs Extend Beyond Thicknesses of Lateral Side Plates

The height, H, of each egg-shaped bone contacting element 400 can be measured from its top end 412 on the superior side portion 410 to the flatter bottom end 442 on the inferior side portion 440.

For example, referring to FIG. 3, the sequentially increasing heights ($H_1$, $H_2$, and $H_3$) of three neighboring egg-shaped bone contacting elements 400 along longitudinal row, $LR_1$, are shown. Similarly, referring to FIG. 4, the sequentially increasing heights ($H_4$, $H_5$, and $H_6$) of three neighboring egg-shaped bone contacting elements 400 along transverse row, $TR_1$, are shown.

Moreover, the thickness, T, of each of the first lateral side plate 156 and the second lateral side plate 158 can be measured between their respective top and bottom surfaces. The thicknesses of both the first lateral side plate 156 and the second lateral side plate 158 are less than each of the heights ($H_1$, $H_2$, $H_3$, etc.) of the egg-shaped bone contacting elements 400 making up implant 100. More importantly, the superior side portion 410 of each bone contacting element 400 extends above the top surfaces of the first and second lateral side plates 156, 158. Moreover, the inferior side portion 440 of each bone contacting element 400 extends below the bottom surfaces of the first and second lateral side plates 156, 158.

As a result of the geometry between the egg-shaped bone contacting elements 400 and the first and second lateral side plates 156, 158, when implant 100 is initially implanted substantially all weight bearing is born by the superior side portions 420 and inferior side portions 440 of the bone contacting elements 400. The peripheral structure 150 of implant 100 is essentially a non-factor with respect to initial weight bearing and during at least the initial stages of subsidence. That is, substantially all weight bearing is accomplished by the interior architecture 104 of implant 100 of the present teachings. As subsidence continues, the first and second lateral side plates 156, 158 can begin to bear weight thereby controlling subsidence in a step-like fashion. According to various embodiments, the interior architecture 104 is structurally strong and doesn't rely on a peripheral structure 150 for structural rigidity. Moreover, the sizing and shape of the egg-shaped bone contacting elements 400 making up the interior architecture 104 allows bone fusion to occur beyond the posterior and anterior sides of implant 100.

Implant Subsidence Control

It is known that implants subside or settle with the onset of weight before bone fusion can start. Some level of settling occurs as no implant perfectly fits the space between any two vertebral end plates. As will be discussed in more detail below, to improve bone fusion, implant 100 of the present teachings can bear more weight and provide improved subsidence control by way of the shape of the egg-shaped bone contacting elements 400 of the present teachings.

More particularly, the egg-shaped bone contacting elements 400 of implant 100 achieve unequal load bearing between the superior side 130 and the inferior side 140 of implant 100. The top end 412 of each egg (that is, the pointy side having the smallest arc radius) cuts through the surface of the upper vertebral end plate quicker than the flatter bottom end 442 cuts through the lower vertebral end plate. Since the bottom end 442 of each bone contacting element 400 is flatter, broader, and more rounded compared to the top end 412, it possesses a larger surface area which allows it to bear more weight and improves bone fusion. This asymmetric weight bearing is achieved since the superior side 130 of implant 100 bites into bone more than the inferior side 140 after implantation.

The egg-shaped bone contacting elements 400 also provide selective subsidence control (i.e. settling) during the 3-4-month healing process. Selective subsidence control of the upper vertebral end plate compared to the lower end plate is also achieved by the top ends 412 of the eggs having a smaller arc radius compared to the bottom ends 442. Initially, the top end 412 of each egg-shaped bone contacting element 400 engages the upper vertebral end plate with a relatively small surface area of contact. However, the surface area gradually increases with more weight bearing as the upper end plate cuts and rides down the superior side portions 410 of the bone contacting elements 400. In this manner, the top ends 412 of the eggs provide a more controlled settling by initially breaking through the upper vertebral end plate and then providing a progressively increased settling resistance. The egg-shape of the bone contacting elements 400 results in a slowly increasing contacted surface area as settling progresses thereby providing the progressive controlled resistance to subsidence.

Since settling occurs around a center of axis of rotation in a circular fashion, it is desirable for implant 100 to subside with the top vertebral end plate settling downwardly towards the bottom vertebral end plate. The top ends 412 and the bottom ends 442 of each of the egg-shaped bone contacting elements 400 making up the interior architecture 104 spread the weight bearing over many surfaces and increase the surface area of contact. The top ends 412, and to a lesser extent the bottom ends 442, of each of the egg-shaped bone contacting elements 400 progressively and selectively cut into and bear weight to better promote bone fusion.

Differential Doming

The domed shape of the superior contour surface 460 of implant 100 is substantially different from the domed shape of the inferior contour surface 480. The doming of these surfaces 460, 480 can be customized to match as closely as possible the corresponding geometries of the opposing (i.e. upper and lower) vertebral end plates at the desired spinal location of implantation.

The surface contours of the domed surfaces 460, 480 of implant 100 can be customized by scaling or staggering the sizes of neighboring egg-shaped bone contacting elements 400. As discussed above, the superior side portions 410 of the plurality of egg-shaped bone contacting elements 400 together form the superior contour surface 460 and the inferior side portions 440 of the plurality of egg-shaped bone contacting elements 400 together form the inferior contour surface 480. By sequentially altering or staggering the heights, H, of neighboring egg-shaped bone contacting elements 400 along any respective row (for example, along a longitudinal row or a transverse row), the contour of the domed surfaces 460, 480 can be altered and customized based on the ultimate location of implantation. That is, the contour of the domed surfaces 460, 480 in a direction from the anterior side 110 to the posterior side 112 of the implant 100, or in a direction from the first lateral side 114 to the second lateral side 116, can be controlled by scaling the sizes of neighboring egg-shaped bone contacting elements 400.

For example, referring to FIG. 3, doming along the longitudinal dimension of implant 100 can be achieved by having the heights, ($H_1$, $H_2$, $H_3$), of the bone contacting elements 400 in each longitudinal row, LR, sequentially increase in a direction toward the median plane. In this example, the egg-shaped bone contacting element 400 located at the middle of each longitudinal row, LR, would possess the largest height and represent the apex of the domed surface in the longitudinal dimension on the superior side 130 of implant 100.

For another example, referring to FIG. 4, doming along the transverse dimension of implant 100 can be achieved by having the heights, ($H_4$, $H_5$, and $H_6$), of the bone contacting elements 400 in each transverse row, TR, sequentially increase in a direction from the posterior side 112 of implant 100 to the anterior side 110 of implant 100. In this example, the egg-shaped bone contacting element 400 on the anterior side 110 of each transverse row, TR, would possess the largest height and represent the apex of the domed surface in the transverse dimension on both the superior side 130 and inferior side 140 of implant 100.

Referring to FIGS. 2 and 4, outwardly domed surfaces of implant 100 can also be provided on the posterior side 112 of implant 100 by implementing a posterior cross-member 152 that bows outwardly in a posterior direction. As shown in FIG. 4, an outer surface of the posterior cross-member 152 can be arranged to substantially match the curved exterior shape of the intermediate side portions 420 of the eggs 400 in the first longitudinal row, $LR_1$.

Similarly, an outwardly domed surface can be achieved on the anterior side 110 of implant 100 by implementing an anterior cross-member 154 that bows outwardly in an anterior direction. As shown in FIG. 4, an outer surface of the anterior cross-member 154 can be arranged to substantially match the curved exterior shape of the intermediate side portions 420 of the eggs 400 in the third longitudinal row, $LR_3$.

By incorporating outwardly bowed posterior cross-member 152 and anterior cross-member 154 that match the shape of the egg-shaped bone contacting elements 400, the width of implant 100 is maximized along the posterior-anterior axis 122 thereby increasing fusion area in that dimension.

Accordingly, the exterior surface contours of implant 100 that includes ovate or egg-shaped bone contacting elements 400 can be domed in various dimensions. Doming along several dimensions allows for a bigger implant fitting into the same space between neighboring vertebral end plates, promotes better contact with end plates from above and below (increasing fusion area), and promotes self-centering as implant 100 seeks the center of each of the top and bottom domed surfaces of neighboring vertebral end plates. Moreover, the domed surface contours can prevent the need for retaining screws and may reduce lateral rejection of the implant when inserted laterally.

While the implant 100 shown in FIGS. 1-4 above could generally be used in conjunction with an LLIF (Lateral Lumbar Interbody Fusion) or an OLIF (Oblique Lateral Interbody Fusion) procedure, an implant including the structural features of the present teachings can be shaped to promote spinal entry from any direction or shaped for implantation at various spinal locations including cervical, thoracic, anterior lumbar, posterior lumbar, lateral lumbar, etc. The same structural principles apply to the architecture of the ovate or egg-shaped bone contacting elements 400 no matter the direction of spinal entry or the implantation location of the fusion device. This can allow for a custom 3-D printed implant including egg-shaped bone contacting elements 400 for any specific situation.

Additional Embodiments

In different embodiments, the dimensions of an implant can vary. Exemplary dimensions that could be varied include length, width and thickness of the overall implant. Moreover, the scaling of the dimensions of one or more egg-shaped bone contacting elements of the implant could vary from one embodiment to another.

FIGS. 5-9 show another embodiment of an implant 700. Implant 700 can be similar in many ways to implant 100 discussed above in relation to FIGS. 1-4. In some embodiments, implant 700 can have a greater width and/or length (and thus a larger overall footprint) than implant 100 of the first embodiment. However, the structural features of the plurality of ovate or egg-shaped bone contacting elements 400 making up the interior implant architecture 704 of the implant 700 are substantially similar.

Figure 6:
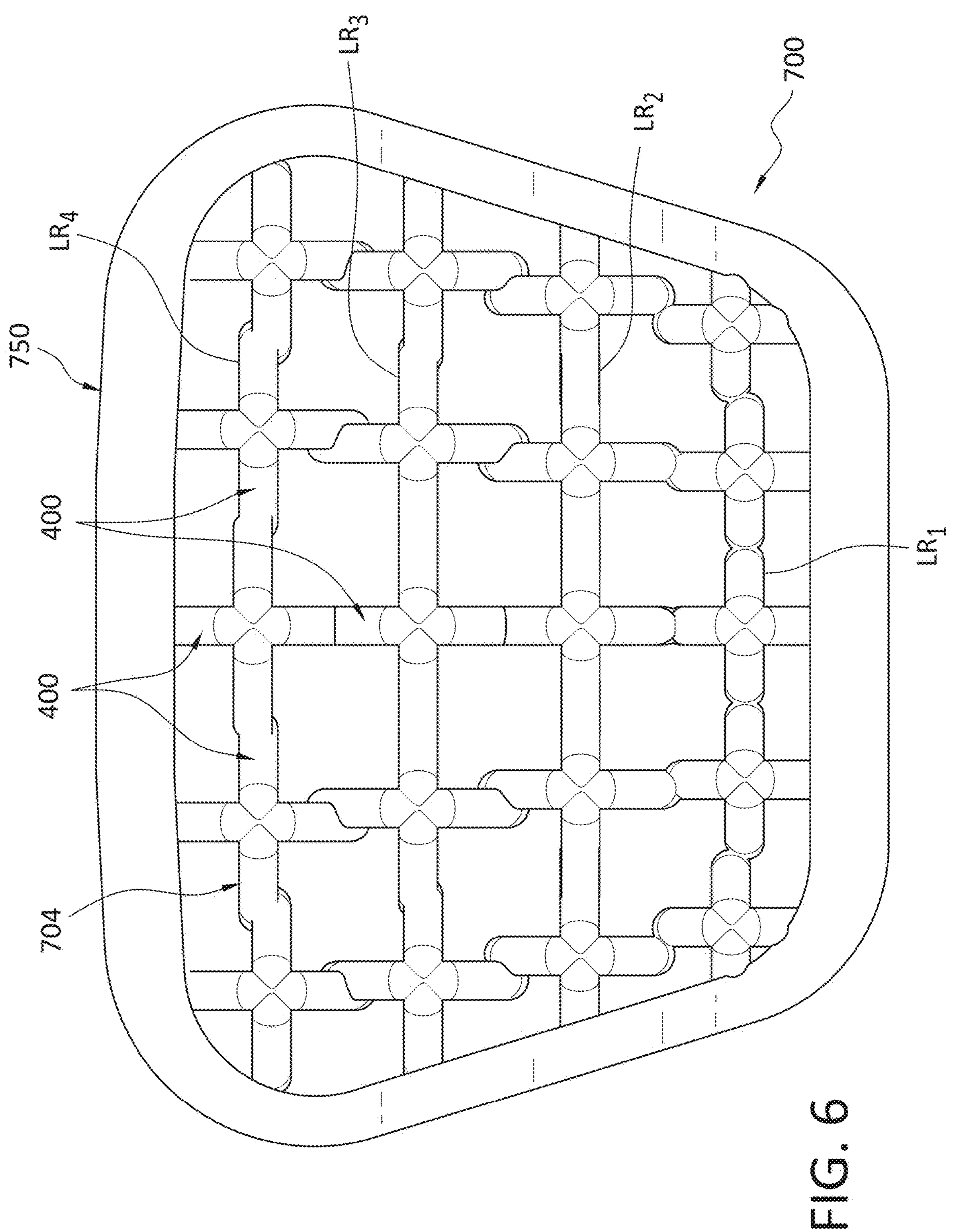
FIG. 6 is a top view of the implant of FIG. 5.
Figures 7, 8:
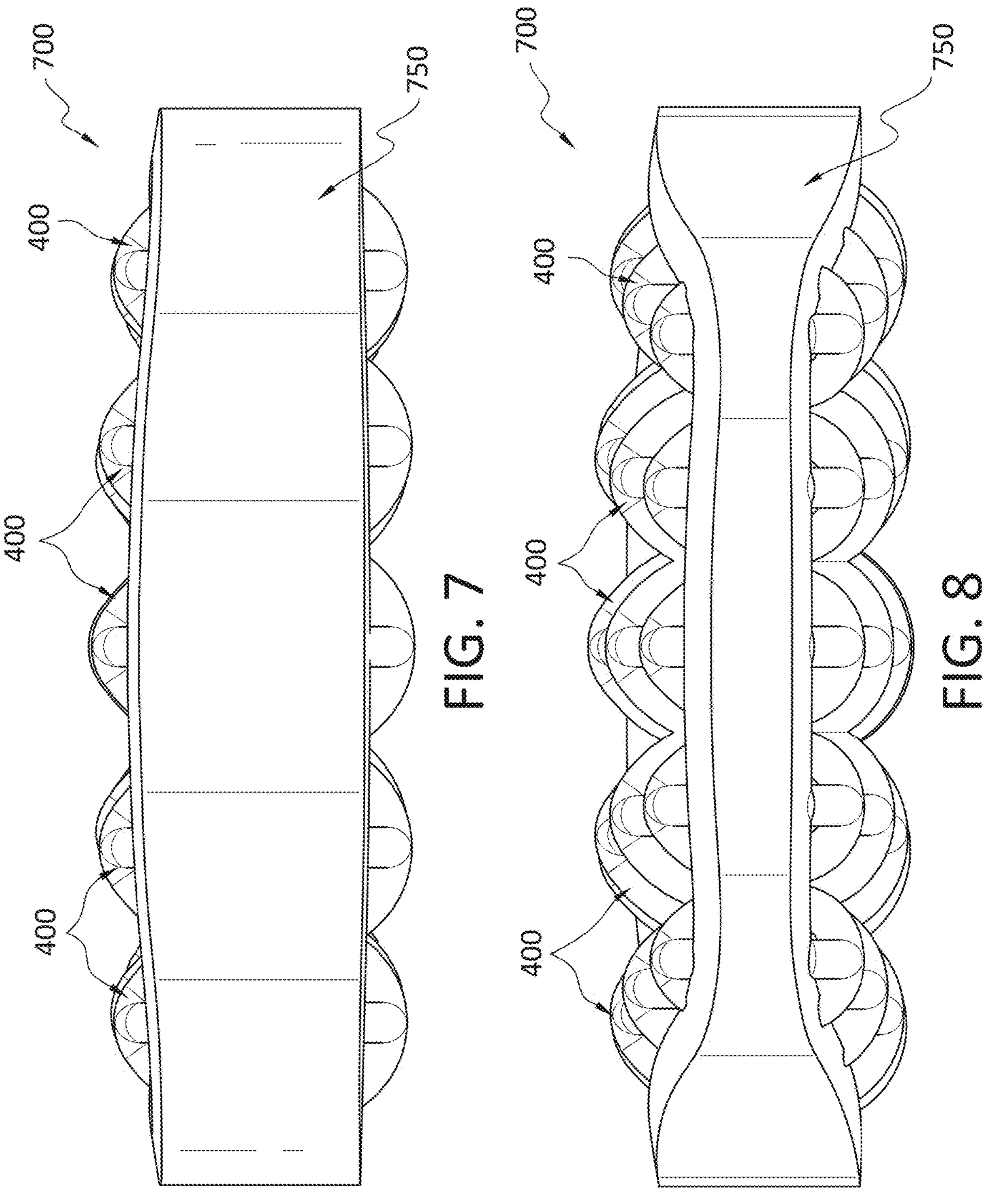
FIG. 7 is a front view (anterior) or back view (posterior) of the implant of FIG. 5.
FIG. 8 is a back view (posterior) or front view (anterior) of the implant of FIG. 5.
Figure 9:
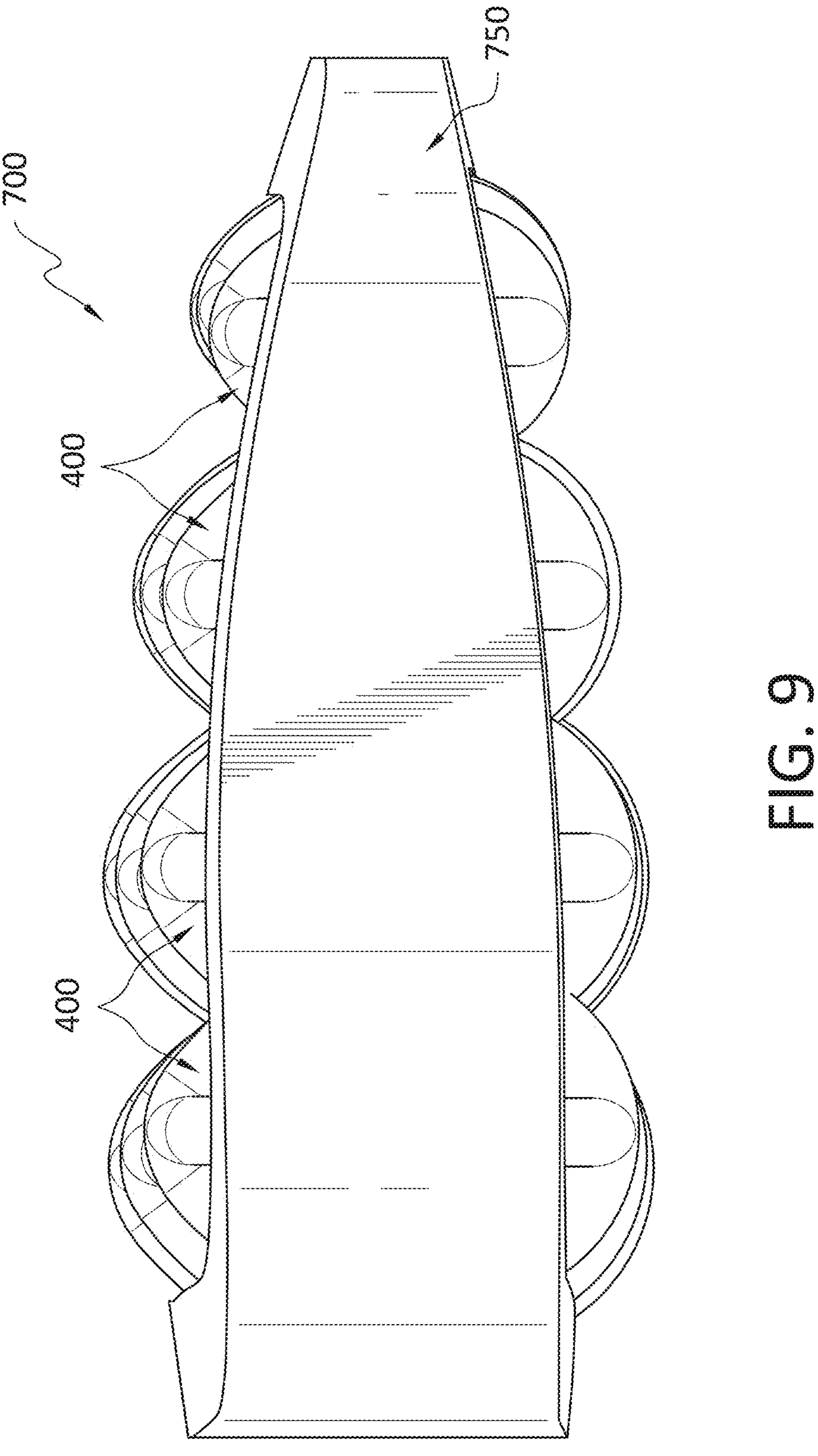
FIG. 9 is a side or lateral view of the implant of FIG. 5.

For example, referring to FIG. 6, the ring forming the peripheral structure 750 of this embodiment forms a general trapezoidal shape. This type of implant 700 can be used in conjunction with an ALIF (Anterior Lumbar Interbody Fusion) procedure. Implant 700 incorporates the same egg-shaped bone contacting architecture 704 but in a different arrangement, size, and envelope to allow implantation from the anterior (or front direction). To accommodate the larger width of the trapezoidal shape of the implant 700, the interior implant architecture 704 of this embodiment includes an additional longitudinal row, $LR_4$, of egg-shaped bone contacting elements 400 along the transverse dimension of the implant.

As discussed above with respect to the implant of the first embodiment, no matter the direction from which the spine is assessed, the implant 100, 700 of the present teachings can be provided with a threaded feature for attachment to an insertion tool, as well as pin holes to keep the clocking alignment. That is, the pin holes can allow temporary fixation by accommodating temporary fixation pins, which are used to hold the implant in its desired position on the vertebrae during the preliminary stages of surgery.

Bone Growth Promoting Material

In some embodiments, bone growth can be facilitated by applying a bone growth promoting material in or around portions of implant 100, 700. As used herein, a "bone growth promoting material" (or BGPM) is any material that helps bone growth. Bone growth promoting materials may include provisions that are freeze dried onto a surface or adhered to the metal through the use of linker molecules or a binder.

Manufacturing and Materials

The various components of an implant can be fabricated from biocompatible materials suitable for implantation in a human body, including but not limited to, metals (e.g. titanium or other metals), synthetic polymers, ceramics, and/or their combinations, depending on the particular application and/or preference of a medical practitioner.

In different embodiments, processes for making an implant can vary. In some embodiments, the entire implant can be manufactured and assembled via injection-molding, cast or injection molding, insert-molding, co-extrusion, pultrusion, transfer molding, overmolding, compression molding, 3-Dimensional (3-D) printing, dip-coating, spray-coating, powder-coating, porous-coating, milling from a solid stock material and their combinations.

Goals of Implant

With implant 100, 700 of the present teachings, the amount of bone growth can be increased on average of 30-40% compared to current implants on the market. The incorporation of egg-shaped bone contacting elements 400 progressively controls subsidence which promotes viable bone growth that helps to provide more viable outcomes in the long term. By increasing the surface contact area and putting contact points across the entire dome-shaped interiors of the vertebral end plates, the interior architecture 104 controls the weight bearing across the entire implant promoting bone growth.

Interior architecture 104, 704 including egg-shaped bone contacting elements 400 provides a structurally strong implant that can support neighboring vertebral end plates without additional structural support such as perimeter walls. Interior architecture 104, 704 allows bone growth to creep out from the anterior and posterior sides of implant 100.

Moreover, the domed shape of the outer surfaces of implant 100, 700 allows engagement to begin at the middle of the dome and helps prevent lateral ejection after implantation.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

What is claimed is:

1. A surgical implant comprising:

an interior architecture including at least one egg-shaped bone contacting element, the at least one egg-shaped bone contacting element being defined by a first wall structure including a superior side portion, intermediate portions, and an inferior side portion;

wherein the superior side portion includes a top end defining a first arc radius and the inferior side portion includes a bottom end defining a second arc radius, whereby the first arc radius is smaller than the second arc radius; and wherein the at least one egg-shaped bone contacting element includes a height measured from the top end to the bottom end of the first wall structure and a width at a maximum distance measured directly across the intermediate portions, whereby the height is greater than the width.

2. A surgical implant comprising:

an interior architecture including at least one egg-shaped bone contacting element, the at least one egg-shaped bone contacting element being defined by a first wall structure including a superior side portion, intermediate portions, and an inferior side portion;

wherein the superior side portion includes a top end defining a first arc radius and the inferior side portion includes a bottom end defining a second arc radius, whereby the first arc radius is smaller than the second arc radius; and wherein the top end of the at least one egg-shaped bone contacting elements is capable of cutting into a surface of an upper vertebral end plate and the bottom end of the at least one egg-shaped bone contacting elements is capable of cutting into a surface of a lower vertebral end plate.

3. A surgical implant comprising:

an interior architecture including at least one egg-shaped bone contacting element, the at least one egg-shaped bone contacting element being defined by a first wall structure including a superior side portion, intermediate portions, and an inferior side portion;

wherein the superior side portion includes a top end defining a first arc radius and the inferior side portion includes a bottom end defining a second arc radius, whereby the first arc radius is smaller than the second arc radius; and wherein the interior architecture includes a plurality of egg-shaped bone contacting elements arranged in a three-dimensional structure, the plurality of egg-shaped bone contacting elements each including a superior side portion and an inferior side portion, whereby the superior side portions of the egg-shaped bone contacting elements form a domed superior contour surface and the inferior side portions of the egg-shaped bone contacting elements form a domed inferior contour surface, and the domed superior contour surface is shaped differently from the domed inferior contour surface.

4. A surgical implant comprising:

an interior architecture including at least one egg-shaped bone contacting element, the at least one egg-shaped bone contacting element being defined by a first wall structure including a superior side portion including a top end, intermediate portions, and an inferior side portion including a bottom end;

wherein the at least one egg-shaped bone contacting element includes a height measured from the top end to the bottom end of the first wall structure and a width measured at a maximum distance directly across the intermediate portions, whereby the height is greater than the width; and wherein the bottom end is broader compared to the top end.

5. A surgical implant comprising:

an interior architecture including at least one egg-shaped bone contacting element, the at least one egg-shaped bone contacting element being defined by a first wall structure including a superior side portion including a top end, intermediate portions, and an inferior side portion including a bottom end;

wherein the at least one egg-shaped bone contacting element includes a height measured from the top end to the bottom end of the first wall structure and a width measured at a maximum distance directly across the intermediate portions, whereby the height is greater than the width; and wherein the superior side portion of the at least one egg-shaped bone contacting element is capable of cutting into a surface of an upper vertebral end plate and the inferior side portion of the at least one egg-shaped bone contacting elements is capable of cutting into a surface of a lower vertebral end plate.

6. A surgical implant comprising:

an interior architecture including at least one egg-shaped bone contacting element, the at least one egg-shaped bone contacting element being defined by a first wall structure including a superior side portion including a top end, intermediate portions, and an inferior side portion including a bottom end;

wherein the at least one egg-shaped bone contacting element includes a height measured from the top end to the bottom end of the first wall structure and a width measured at a maximum distance directly across the intermediate portions, whereby the height is greater than the width; and wherein the interior architecture includes a plurality of egg-shaped bone contacting elements arranged in a three-dimensional structure, the plurality of egg-shaped bone contacting elements each including a superior side portion and an inferior side portion, whereby the superior side portions of the egg-shaped bone contacting elements form a domed superior contour surface and the inferior side portions of the egg-shaped bone contacting elements form a domed inferior contour surface, and the domed superior contour surface is shaped differently from the domed inferior contour surface.

7. A surgical implant comprising:

an interior architecture including a plurality of egg-shaped bone contacting elements arranged in a three-dimensional structure, the plurality of egg-shaped bone contacting elements including a superior side portion and an inferior side portion;

wherein the superior side portion of the egg-shaped bone contacting elements form a domed superior contour surface and the inferior side portion of the egg-shaped bone contacting elements form a domed inferior contour surface; and wherein the domed superior contour surface is shaped differently from the domed inferior contour surface.

8. The surgical implant of claim 7, wherein the superior side portion of at least one egg-shaped bone contacting element includes a top end defining a first arc radius and the inferior side portion of at least one egg-shaped bone contacting element includes a bottom end defining a second arc radius, whereby the first arc radius is smaller than the second arc radius.

9. The surgical implant of claim 7, wherein at least one egg-shaped bone contacting element defines a first wall structure that includes a top end on the superior side portion and a bottom end on the inferior side portion, and further defines a second wall structure that intersects the first wall structure and shares the top end and bottom end with the first wall structure.

10. The surgical implant of claim 9, wherein the first wall structure intersects substantially perpendicularly with respect to the second wall structure.

11. The surgical implant of claim 7, wherein the plurality of egg-shaped bone contacting elements includes intermediate portions, and wherein a height measured from a top end of the superior side portion to a bottom end of the inferior side portion and a width measured at a maximum distance directly across the intermediate portions, whereby the height is greater than the width.

12. The surgical implant of claim 7, wherein the superior side portion of the plurality of egg-shaped bone contacting elements is capable of cutting into a surface of an upper vertebral end plate and the inferior side portion of the plurality of egg-shaped bone contacting elements is capable of cutting into a surface of a lower vertebral end plate.

13. A surgical implant comprising:

an interior architecture including at least one ovate-shaped bone contacting element, the at least one ovate-shaped bone contacting element being defined by a first wall structure including a superior side portion, intermediate portions, and an inferior side portion;

wherein the superior side portion includes a top end and the inferior side portion includes a bottom end and the bottom end is broader compared to the top end; and wherein the superior side portion of the at least one ovate-shaped bone contacting element is capable of cutting into a surface of an upper vertebral end plate and the inferior side portion of the at least one ovate-shaped bone contacting element is capable of cutting into a surface of a lower vertebral end plate.

* * * * *